(12) United States Patent
Mulder

(10) Patent No.: US 7,921,849 B2
(45) Date of Patent: Apr. 12, 2011

(54) CONDOM APPLICATOR

(76) Inventor: Roelof Mulder, Cape Town (ZA)

( * ) Notice: Subject to any disclaimer, the term of this patent is extended or adjusted under 35 U.S.C. 154(b) by 30 days.

(21) Appl. No.: 11/568,963

(22) PCT Filed: May 3, 2005

(86) PCT No.: PCT/ZA2005/000062
§ 371 (c)(1), (2), (4) Date: Dec. 2, 2006

(87) PCT Pub. No.: WO2005/107663
PCT Pub. Date: Nov. 17, 2005

(65) Prior Publication Data
US 2007/0225549 A1 Sep. 27, 2007

(30) Foreign Application Priority Data

May 12, 2004 (ZA) .................... 2004/3610

(51) Int. Cl.
*A61F 6/02* (2006.01)
*B65D 85/08* (2006.01)
*B65D 85/14* (2006.01)
*A61M 1/00* (2006.01)
*A61F 5/44* (2006.01)

(52) U.S. Cl. ........ 128/844; 128/842; 128/917; 128/918; 604/317; 604/327; 604/346; 604/347; 206/69

(58) Field of Classification Search .................. 128/842, 128/844, 918, 917; 604/327, 346, 347, 317; 206/69
See application file for complete search history.

(56) References Cited

U.S. PATENT DOCUMENTS

| 4,738,357 A | * | 4/1988 | Martin et al. .................... 206/69 |
| 4,875,491 A | | 10/1989 | Parrone et al. |
| 5,163,449 A | * | 11/1992 | van der Valk ................. 128/844 |
| 5,316,019 A | | 5/1994 | Jones et al. |
| 5,606,982 A | * | 3/1997 | Piotti ............................ 128/842 |
| 5,651,374 A | * | 7/1997 | Wester .......................... 128/844 |
| 5,862,908 A | * | 1/1999 | Arbin ............................ 206/69 |

FOREIGN PATENT DOCUMENTS

| WO | WO 96/08220 | 3/1996 |
| WO | WO 99/32058 | 7/1999 |
| WO | WO 02/069861 | 9/2002 |

* cited by examiner

*Primary Examiner* — Patricia M Bianco
*Assistant Examiner* — Brandon Jackson
(74) *Attorney, Agent, or Firm* — Stites & Harbison PLLC; Douglas E. Jackson

(57) ABSTRACT

A condom applicator (10) is disclosed which comprises a base (12) with a split line (18) across it and two flaps (14) which are connected by flimsy hinges to the base (12). Tubs (16) protrude from the flap (14). The base (12) includes two generally parallel walls (24, 28) and a base (26) which bound a trough (22). The trough receives the hem ring of a condom. There is an opening in the base which is encircled by the inner wall (24). When the flaps (14) are folded over, areas (44) of the flaps (14) cover the trough leaving a gap (G) between the wall (24) and the area (44). The tubs (16) span across said opening. The teat of the condom lies across the opening.

16 Claims, 8 Drawing Sheets

CONDOM APPLICATOR

This application is a national stage entry under 35 U.S.C. 371 of international application PCT/ZA2005/000062, filed 3 May 2005 which claims priority to South African patent application ZA 2004/3610, filed 12 May 2004, the specifications of which are hereby incorporated herein by reference.

FIELD OF THE INVENTION

THIS INVENTION relates to condom applicators.

BACKGROUND TO THE INVENTION

The problems inherent in the application of condoms, and in known applicators, are discussed in WO 02/069861A1. This PCT specification discloses an applicator which is an improvement on those disclosed in the art represented by, for example, U.S. Pat. No. 4,875,491.

The present invention seeks to provide a still further improved condom applicator.

BRIEF DESCRIPTION OF THE INVENTION

According to one aspect of the present invention there is provided a condom applicator which comprises a base comprising at least two separable parts, each part having a section of a trough therein and the trough sections of the parts together defining an upwardly open trough for receiving the hem ring of a condom, the trough having an inner circumferentially extending wall and an outer circumferentially extending wall and at least two flaps having areas which cover the trough whilst leaving a circumferentially extending gap between said inner circumferentially extending wall and edges of the flaps.

The trough is preferably circular in plan but it can also be oval.

Said applicator preferably comprises two base parts held together by one or more frangible bridges, each part having one half of the trough therein.

Said flaps are preferably connected to said base parts by film hinges.

Said inner and outer walls of the trough preferably diverge so that the trough is wider at its mouth than at its base. Either both walls can slope or one can be vertical and the other can slope.

Said area of each flap can be below the level of the remainder of each flap, there being inclined walls joining said areas and said remainders.

The upper edge of said inner wall is preferably at a level above that of said area of the flap whereby said gap is defined between the edges of the flaps and the outwardly facing surface of said inner wall.

Tabs for holding the condom's nipple in a compressed condition can be provided. The tabs can be connected to the flaps by film hinges and can lie across the opening in the applicator which is bounded by the inner wall of the trough. The tabs can each extend fully across said opening or part way across the opening.

The applicator can comprise two separate parts forming a base and two separate flap parts, there being means for enabling each base part to be secured to one of the flap parts.

In a modification of this form said two base parts are connected together by frangible bridges and the two flap parts are connected together by frangible bridges.

The connecting mean preferably comprises locking tabs which fit into sockets.

According to a further aspect of the present invention there is provided, in combination, an applicator as defined above and a condom, the hem ring of the condom being in said trough and the side wall of the condom being in said gap with the nipple end of the condom extending across the opening in the applicator bounded by said inner wall.

According to another aspect of the present invention there is provided a package comprising two pieces of material each piece of material being a laminate of an aluminium foil with synthetic plastics material on each side thereof, said pieces being heat sealed around the edges thereof and there being registering lines of perforations across the outer layers of plastic and nicks in the material at the ends of these lines.

The laminate is preferably polyester, for the outer layer, aluminium and then polythene for the inner layer.

BRIEF DESCRIPTION OF THE DRAWINGS

For a better understanding of the present invention, and to show how the same may be carried into effect, reference will now be made, by way of example, to the accompanying drawings in which:-

DETAILED DESCRIPTION OF THE DRAWINGS

Figure 1:
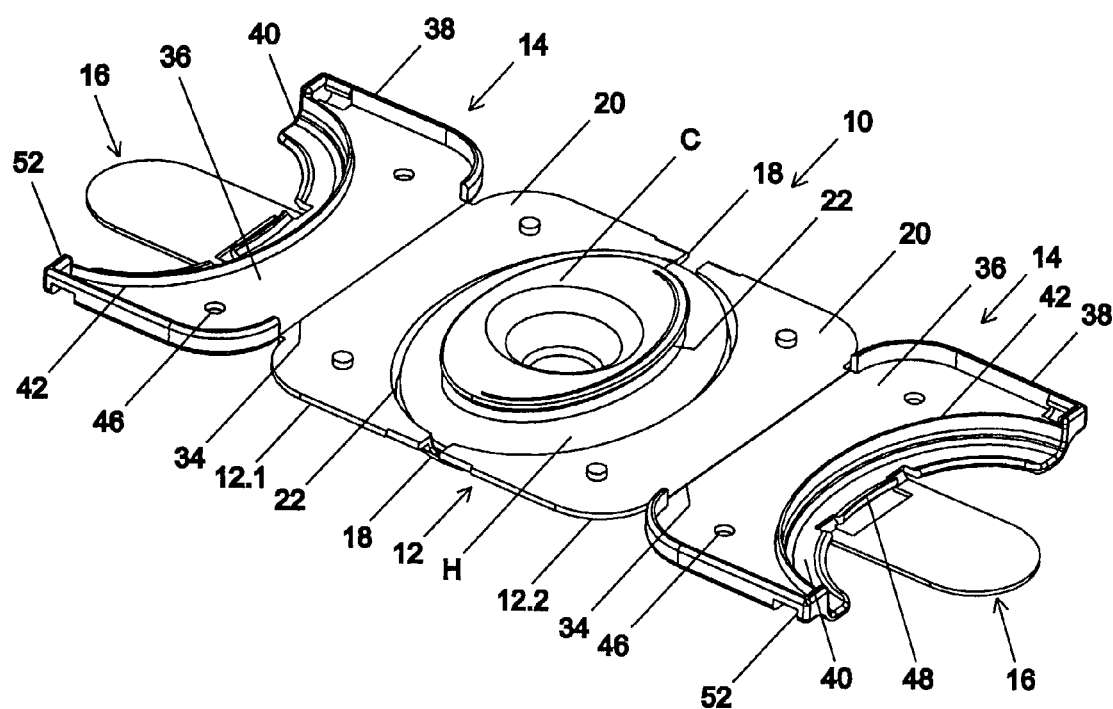
FIG. 1 is a pictorial view of an unfolded condom applicator.

Referring firstly to FIGS. 1 to 4, the applicator 10 comprises a base designated 12, two flaps 14 and two tabs 16.

The base 12 is moulded in two parts 12.1 and 12.2 with a split line 18 between them. To ensure that the parts 12.1 and 12.2 do not separate during packaging of the condom, thin webs (not shown) can bridge the split line 18. These provide insignificant resistance to breaking along the line 18 when such action is required.

The base 12 comprises two planar sections 20 each of which incorporates a semi-circular trough 22. Each trough 22 is bounded by a radially inner wall 24 (see particularly FIG. 4), by a base wall 26 and by a radially outer wall 28. The wall 24 projects above the level of the section 20. The wall 24 slopes radially inwardly and the wall 28 slopes radially outwardly. Thus the base 26 of the trough, measured radially, is narrower than the mouth of the trough measured in the same direction.

Interlocking pins 30 protrude upwardly from the sections 20 and a strengthening rim 32 extends around the outer edge of the lower surface of the base 12.

The flaps 14 are joined to the edges of the parts 12.1, 12.2 remote from the trough 22 by way of film hinges 34. Each flap comprises a planar area 36. One edge of each area 36 is joined by the film hinge 34 to the base 12. Strengthening flanges 38 protrude upwardly from the areas 36.

Figure 2:
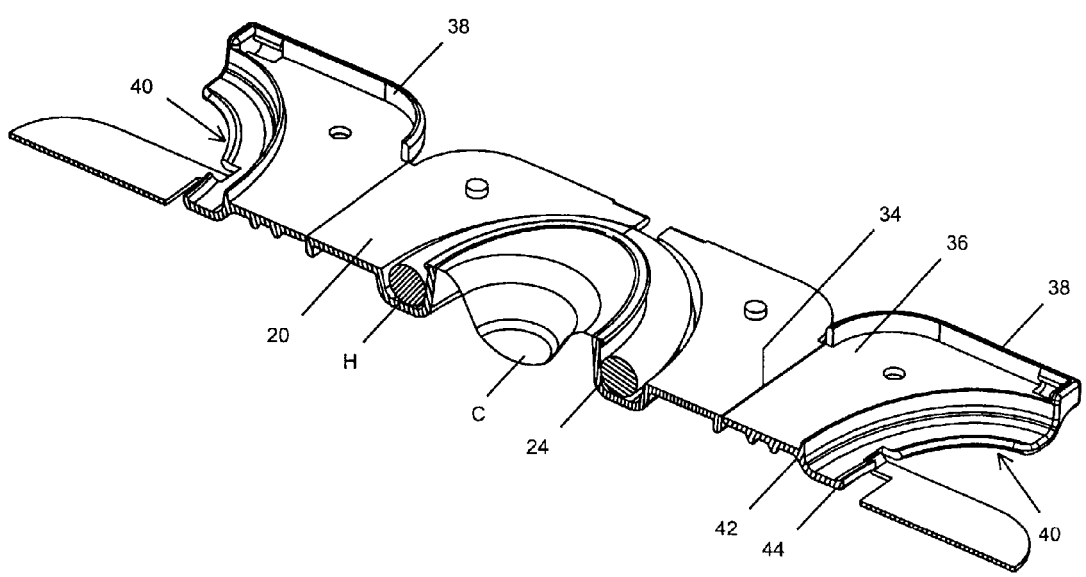
FIG. 2 is a longitudinal section taken along the centre line of the applicator of FIG. 1.
Figure 4:
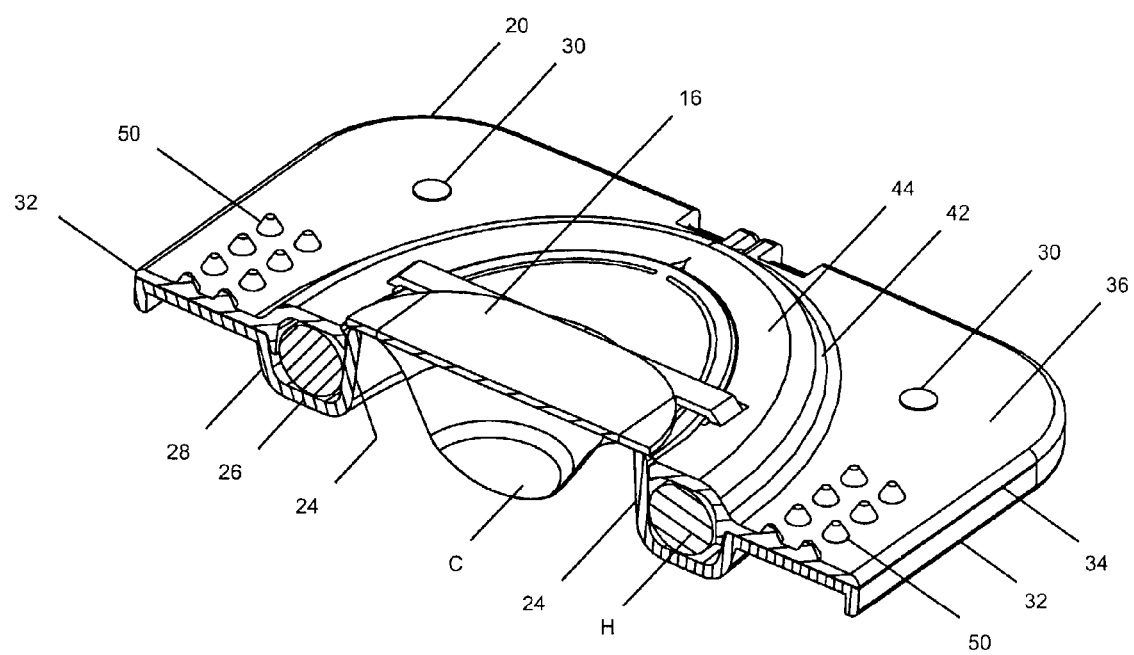
FIG. 4 is a section on the centre line of the folded condom applicator of FIG. 3.
Figure 5:
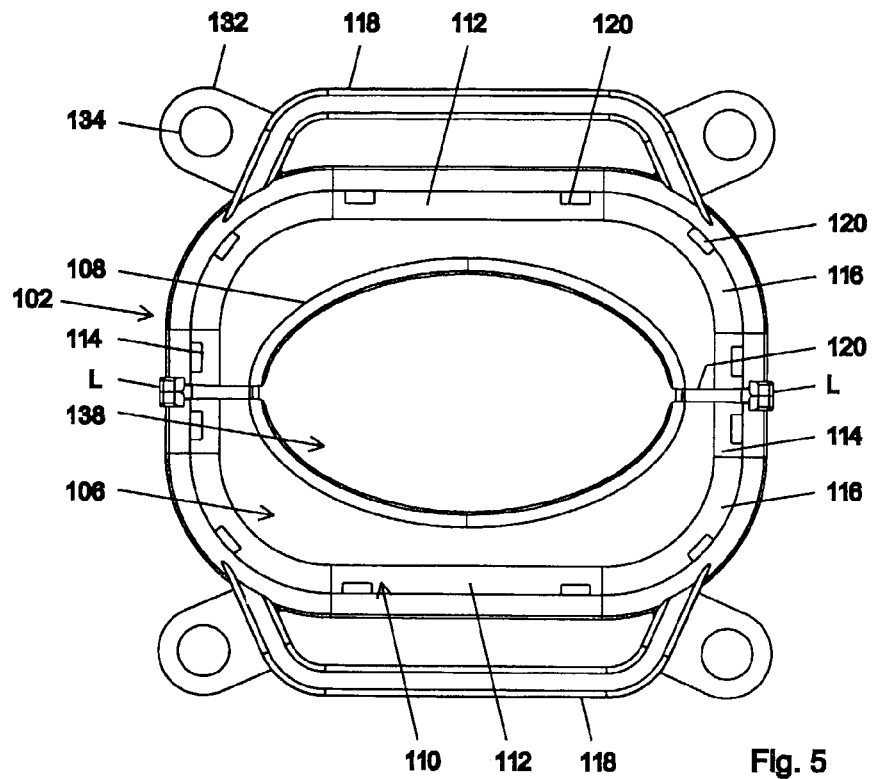
FIG. 5 is a top plan view of one part of a further condom applicator.

Each flap 14 has a semi-circular depression 40 along its remaining edge. The depression comprises a circumferentially extending semi-circular inclined wall 42 and a semi-circular flat area 44 which are best seen in FIGS. 2 and 4.

Sockets 46 are provided in the areas 36, the sockets serving to receive the pins 30.

The tabs 16 are connected to the flaps 14 by way of film hinges 48. It will be noted that the tabs 16 are not shown in FIG. 3.

The underside of each flap 14 (see FIGS. 3 and 4) is dimpled at 50 to provide a finger grip.

Clips are provided at 52 on the flaps 14.

With the applicator as shown in FIGS. 1 and 2, the hem ring H (FIGS. 2 and 4) of a rolled condom C is pressed into the circular trough defined by the two trough halves 22. The closed end of the condom extends across the circular space bounded by the semi-circular inner walls 24 with the nipple at the end of the condom in this space.

Figure 3:
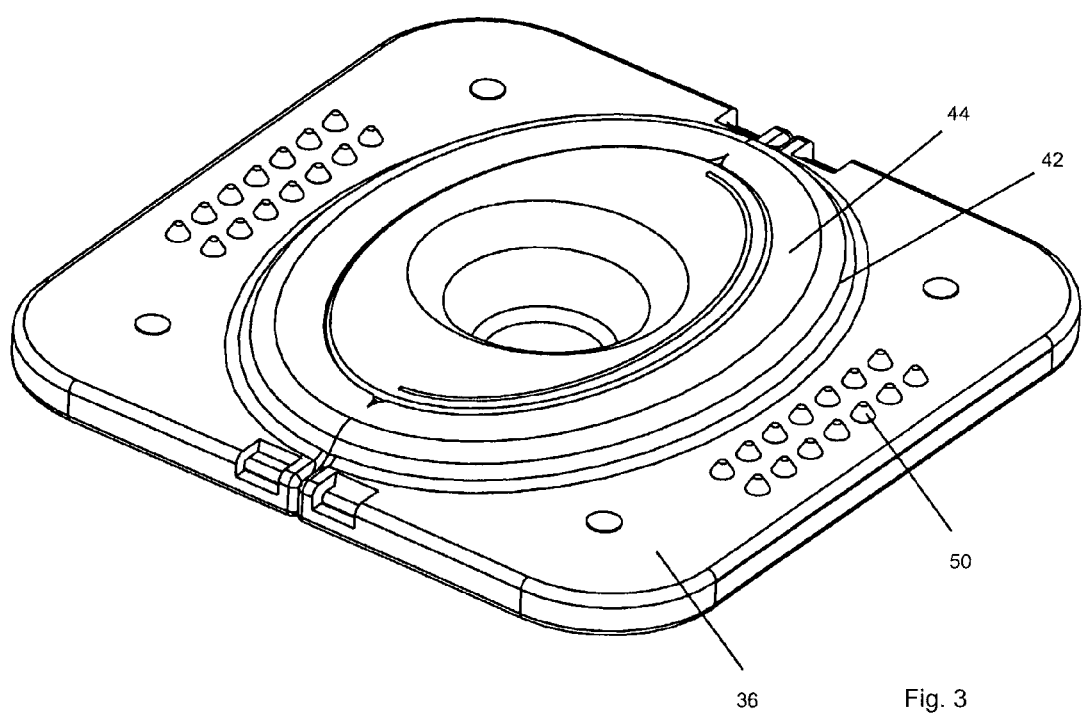
FIG. 3 is a pictorial view of a folded condom applicator.

The flaps 14 are then displaced through 180° to the positions shown in FIGS. 3 and 4. The clips 52 are distorted as the flaps reach their fully folded positions and grip the edges of the parts 12.1, 12.2 thereby to hold the flaps 14 in place. The depressions 40, due to the inversion of the flaps 14, become raised areas and close-off the upwardly open circular trough which contains the hem ring H. The radially inner peripheries of the areas 44 lie close to the radially outer faces of the inner walls 24 of the trough. The condom extends through the circular gap which remains between said inner peripheries and said radially outer faces.

The tabs are pressed down to the positions shown in FIG. 4 and flatten the nipple to prevent air entering it.

Once the applicator has been removed from its package (as will be described hereinafter), the applicator is gripped on each side of the split line. Flexing the applicator causes any flimsy connection between the two parts to fail. Only the hem ring H now holds the two parts together.

As the applicator is slid along the erect penis, the condom unrolls from the hem ring and feeds out through the gap between the inner peripheries of the flaps and the radially outer face of the inner wall of the circular trough.

Turning now to FIGS. 5 to 10, the applicator 100 illustrated comprises two parts which have been designated 102 and 104. The part 102 (FIG. 5) comprises a trough 106 which is bounded on the inside by a wall 108 which is substantially oval in plan view and on the outside by an outer wall 110. The outer wall 110 extends generally parallel to the wall 108 and has long side sections 112 which are straight, short straight end sections 114 and curved sections 116 joining the sections 112 and 114.

Gripping handles 118 protrude outwardly from the wall 110.

Inter-locking tabs 120 are provided which protrude upwardly from the wall 110.

The part 102 can be moulded in halves, the halves abutting along the centre line L. For ease of handling, however, it is preferred that the part 102 be moulded as a single component with flimsy, frangible moulded bridges connections extending across the centre line L.

The part 104 comprises a wall 122 which matches the wall 110 in shape. Sockets 124 in the wall 122 receive the locking tabs 120 protruding from the wall 110.

Inwardly of each half of the wall 122 there is a flap 126 which has an inner edge which is of generally semi-oval shape. A semi-circular cut-out 128 is provided in the edge of each flap 126.

Gripping handles 130 protrude outwardly from the wall 122 and match the handles 118 in shape.

At each end of each handle 118, 130 there is a tab 132 with a circular hole 134 in it. If desired only the part 102 or the part 104, but not both, has tabs 132.

The part 104 can, in the same way as the part 102, be moulded in halves. However it is preferred that it be moulded in one piece with flimsy bridges extending across the line L1.

Figure 10:
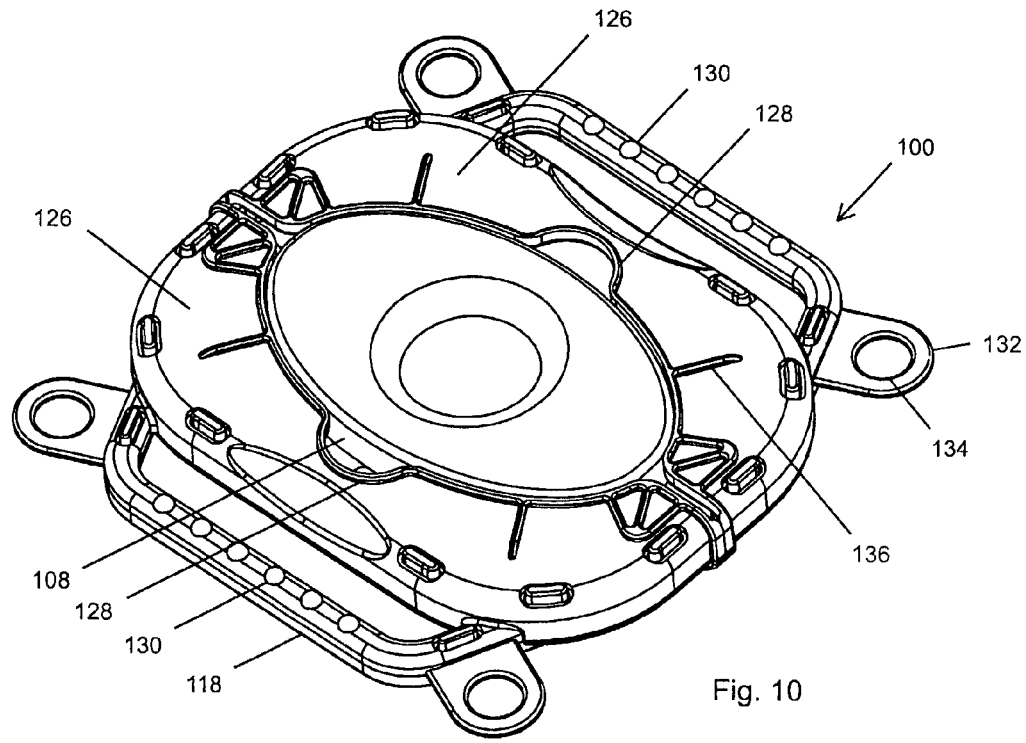
FIG. 10 is a top pictorial view of the assembled applicator.
Figure 11:
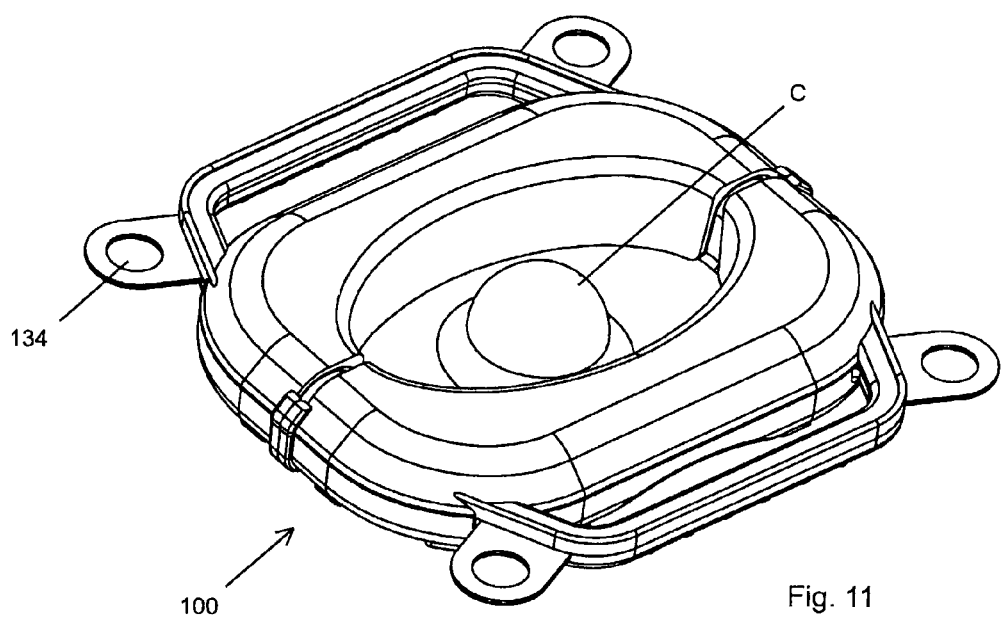
FIG. 11 is a pictorial view of the assembled applicator in an inverted position.

Strengthening ribs 136, which are on the top faces of the flaps 126 as they are viewed in FIG. 10, are provided.

The hem ring H (FIG. 9) of a condom C is pressed into the trough bounded by the walls 108 and 110. If the part 102 is moulded in two halves it is the sightly stretched hem ring which attaches the halves to one another. The nipple of the condom spans across the generally oval opening, designated 138 in FIG. 5, bounded by the inner wall 108.

Figure 6:
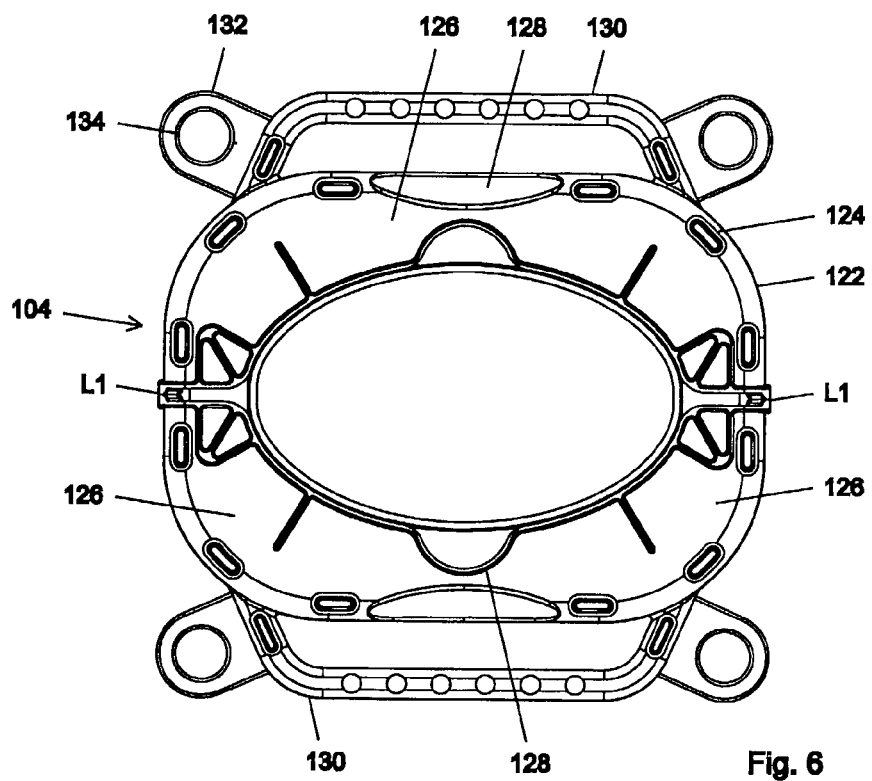
FIG. 6 is a plan view of a further part of the condom applicator, the part being shown inverted from its position of use.
Figure 7:
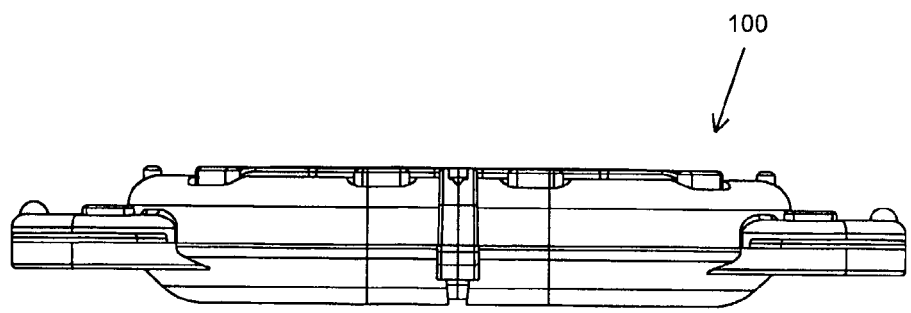
FIGS. 7 and 8 are edge views of the assembled condom applicator.
Figure 8:
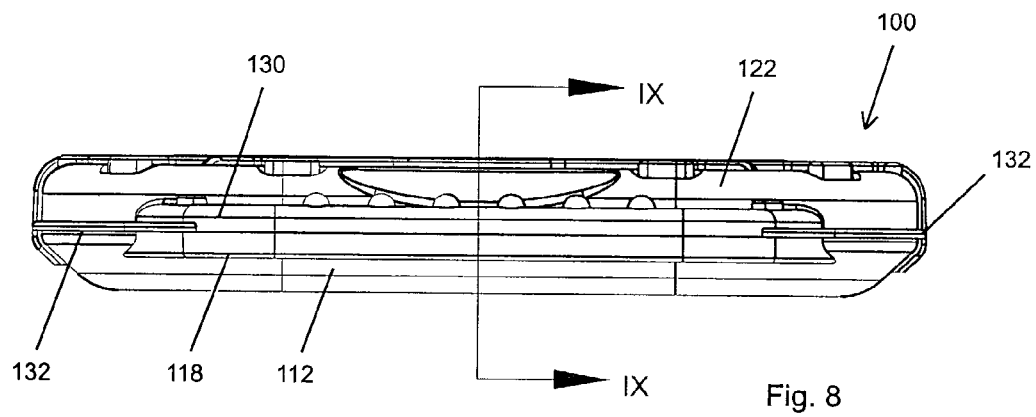

Lubricant can be fed into the trough through the cut-outs 128. The part 104, inverted from the position shown in FIG. 6, is then pressed down onto the part 102. The tabs 120 enter the sockets 124 thereby connecting the parts 102, 104 together.

The flaps 126 cover the trough in which the hem ring is located (see FIG. 9) in the same way that the flaps 14 cover the hem ring trough 22 in FIGS. 1 to 4.

The inner edges of the flaps 126 lie adjacent the wall 108, there being a gap wide enough for that part of the cylindrical wall of the condom adjacent the nipple to pass through.

Figure 9:
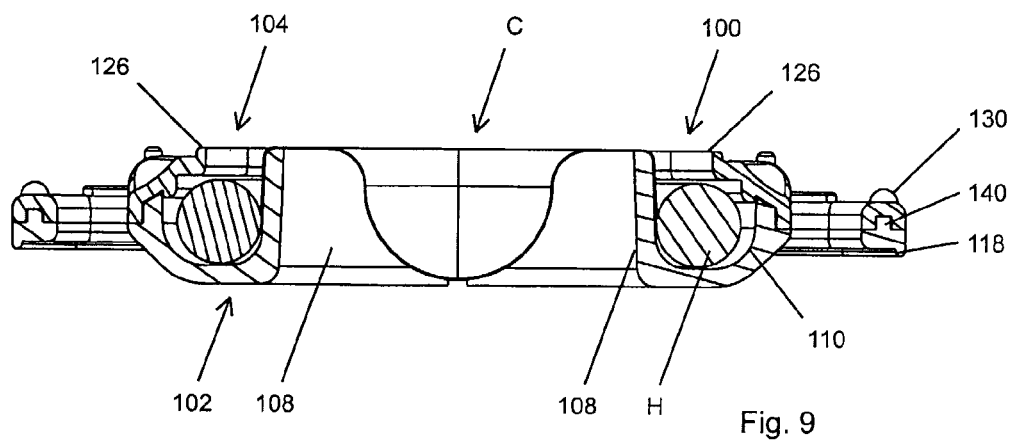
FIG. 9 is a section on the line IX-IX of FIG. 8.

As shown at 140 in FIG. 9, the handles 118, 130 can have tongues and grooves which interlock to secure the handles together.

The condom is applied by flexing the applicator along the registering lines L and L1 and pulling the two halves apart. If there are flimsy connections they break at this stage. The applicator is slid along the penis causing the condom to unroll and feed out of the trough through said gap.

Once the condom is fully unrolled, the two halves are tilted with respect to one another using the handles 118, 130 and simultaneously pulled apart. The hem ring displaces the flaps 126 and comes free of the applicator which is now in two separate halves.

Figure 12:
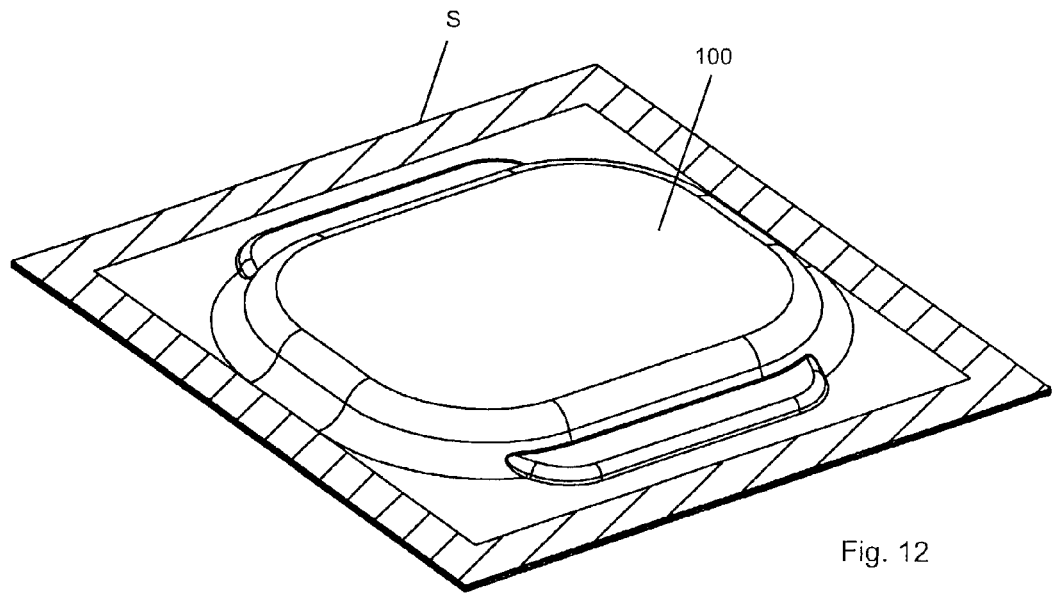
FIG. 12 is a pictorial view of a packaged applicator.
Figure 13:
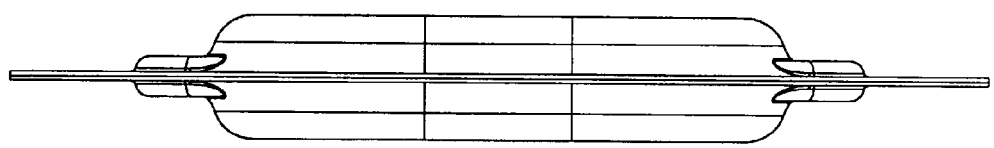
FIGS. 13 and 14 are edge views of the packaged applicator of FIG. 12.
Figure 14:
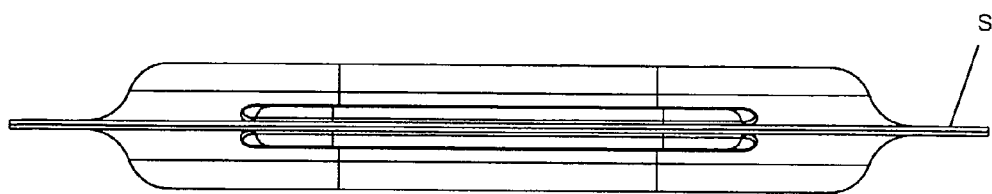

In FIGS. 12 to 14 there is shown a package which contains the applicator of FIGS. 5 to 10. The package comprises a multi-layered foil. In the preferred form the layers are polyester-aluminium-polythene with laminating adhesive between the aluminium and plastics material layers on each side thereof.

The foil is manufactured in strip form and rolled. At intervals along the length of the roll there are transverse lines of perforations. Each perforation can be, for example, 1 mm long with a gap of 1 mm between itself and the next perforation. The perforations are cut partially through the polyester layer but not through the polyethylene or aluminum layers.

At each end of each line of perforations the foil is cut. The cuts are preferably V-shaped and extend inwardly for, for example, 2 mm from the edge of the strip. The perforations thus extend between the cuts.

Two foil strips are fed forward and the applicator placed on the lower of the advancing strips with a line of perforations across the applicator. A heated former, preferably of aluminium, then produces a substantially square seal S which encloses the applicator.

To remove the applicator the package is torn along the line of perforations. The cuts assist in the commencement of the splitting action.

The foils can be sealed through the holes 134 to located the applicator in the package.

The invention claimed is:

1. A condom applicator which comprises:
a base comprising
at least two separable parts, each part having a section of a trough wherein the trough sections of said at least two separable parts together define an upwardly open trough with an open top for receiving a hem ring of a condom, said trough having an inner circumferentially extending wall and an outer circumferentially extending wall, and
at least two flaps having areas which cover respective portions of said open top of said trough, each area of each said flap having an inner edge close to said inner circumferentially extending wall of said part and hence providing a circumferentially extending gap between said inner circumferentially extending wall of said part and said inner edge of said at least two flaps such that after said at least two separable parts are separated in use the condom unrolls from the hem ring and feeds through the circumferentially extending gap.

2. The applicator as claimed in claim 1 wherein said inner circumferentially extending wall and said outer circumferentially extending wall of said trough diverge so that said trough is wider at its mouth than at its base.

3. The applicator as claimed in claim 2, wherein both of said inner circumferentially extending wall and said outer circumferentially extending wall of said trough slope.

4. The applicator as claimed in claim 2, wherein one wall selected from said inner circumferentially extending wall and said outer circumferentially extending wall of said trough is vertical and another slopes.

5. The applicator as claimed in claim 1, and which comprises
two separate base parts forming said base and
two separate flap parts further comprising means for enabling each base part to be secured to one of said two separate flap parts.

6. The applicator as claimed in claim 5 wherein said two base parts are connected together by frangible bridges and said two flap parts are connected together by frangible bridges.

7. The applicator as claimed in claim 5 having tabs and further having sockets, the tabs configured to fit into the sockets wherein the tabs and sockets constitute a securing means.

8. The applicator as claimed in claim 1, and which comprises two base parts held together by one or more frangible bridges, each part selected from said two base parts having one half of said trough therein.

9. The applicator as claimed in claim 8 wherein said at least two flaps are connected to said two base parts by film hinges.

10. The applicator as claimed in claim 1 wherein an area of each flap selected from said at least two flaps is above a level of a remainder of said each flap, there being inclined walls joining said area and said remainder.

11. The applicator as claimed in claim 10 wherein an upper edge of said inner wall is at a level above that of said area of said flap wherein said circumferentially extending gap is defined between edges of said flaps and said outwardly facing surface of said inner circumferentially extending wall.

12. The applicator as claimed in claim 1 and including tabs for holding a condom's nipple in a compressed condition.

13. The applicator as claimed in claim 12, wherein said tabs are connected to said at least two flaps by film hinges and lie across an opening in said condom applicator which is bounded by said inner wall of said trough.

14. The applicator as claims in claim 1, wherein said trough is circular in plan view.

15. The applicator as claimed in claim 1, wherein said trough is oval in plan view.

16. The applicator as claimed in claim 1 further comprising a condom, wherein said hem ring of said condom is in said trough and a side wall of said condom is in said circumferentially extending gap with a nipple end of said condom extending across an opening in said applicator bounded by said inner circumferentially extending wall.

* * * * *